United States Patent
Duncan

(10) Patent No.: US 7,350,519 B2
(45) Date of Patent: Apr. 1, 2008

(54) METHOD AND APPARATUS FOR DELIVERING AN ADDITIVE WITH A CPAP MACHINE

(76) Inventor: Timothy Alan Duncan, 3317 Westmoor Dr., Moorhead, MN (US) 56560

( * ) Notice: Subject to any disclaimer, the term of this patent is extended or adjusted under 35 U.S.C. 154(b) by 510 days.

(21) Appl. No.: 11/001,777

(22) Filed: Dec. 2, 2004

(65) Prior Publication Data

US 2005/0139221 A1    Jun. 30, 2005

Related U.S. Application Data

(60) Provisional application No. 60/532,926, filed on Dec. 29, 2003.

(51) Int. Cl.
*A61M 11/00* (2006.01)
*A61M 15/00* (2006.01)
*A61M 16/00* (2006.01)

(52) U.S. Cl. .................... 128/200.14; 128/204.18; 128/203.12

(58) Field of Classification Search ........... 128/200.14, 128/200.16, 200.19, 200.21, 203.12, 203.16, 128/203.24, 203.26, 204.14, 204.18, 204.21
See application file for complete search history.

(56) References Cited

U.S. PATENT DOCUMENTS

| | | | | |
|---|---|---|---|---|
| 5,231,979 | A | * | 8/1993 | Rose et al. ............ 128/204.14 |
| 5,673,687 | A | * | 10/1997 | Dobson et al. ........ 128/204.14 |
| 6,000,394 | A | * | 12/1999 | Blaha-Schnabel et al. ............ 128/200.19 |
| 6,718,974 | B1 | * | 4/2004 | Moberg ................. 128/204.14 |
| 7,137,388 | B2 | * | 11/2006 | Virr et al. .............. 128/203.17 |
| 2002/0020930 | A1 | * | 2/2002 | Austin et al. ........... 261/119.1 |
| 2003/0053956 | A1 | | 3/2003 | Hofmann |
| 2003/0066526 | A1 | * | 4/2003 | Thudor et al. ......... 128/203.26 |
| 2004/0016432 | A1 | * | 1/2004 | Genger et al. ........ 128/204.18 |
| 2004/0226562 | A1 | * | 11/2004 | Bordewick ............ 128/204.23 |
| 2007/0119454 | A1 | * | 5/2007 | Berthon-Jones et al. ............ 128/204.23 |
| 2007/0125376 | A1 | * | 6/2007 | Reinstadtler ........... 128/203.26 |

FOREIGN PATENT DOCUMENTS

WO    WO 02/089886    * 11/2002

\* cited by examiner

*Primary Examiner*—Teena Mitchell
(74) *Attorney, Agent, or Firm*—Dorsey & Whitney LLP

(57) ABSTRACT

The present invention is a method and apparatus for delivering an additive with a continuous positive airway pressure ("CPAP") machine. The invention includes mixing an additive with humidifier water and providing the additive to the patient with the CPAP machine. According to certain embodiments, the additive can be an aromatic additive or a therapeutic additive.

8 Claims, 2 Drawing Sheets

METHOD AND APPARATUS FOR DELIVERING AN ADDITIVE WITH A CPAP MACHINE

CROSS-REFERENCE TO RELATED APPLICATION(S)

This application claims priority to U.S. Provisional Application No. 60/532,926, filed on Dec. 29, 2003, which is hereby incorporated herein by reference in its entirety.

TECHNICAL FIELD

The present invention relates to treatments for Sleep Apnea. More specifically, the present invention relates to an improved CPAP machine and methods of using a CPAP machine to provide an aromatic or therapeutic additive in the air flow provided to the patient.

BACKGROUND OF THE INVENTION

Approximately twenty million people in the United States have been diagnosed with Sleep Apnea. Sleep Apnea is an over-relaxation of the soft tissue in the back of the throat that causes a cessation of breathing during sleep states. The breathing cessation can cause a lack of oxygen that results in drowsiness and sleep disorders during waking hours.

One treatment for Sleep Apnea is a continuous positive airway pressure ("CPAP") machine, which provides a continuous flow of air through the nostrils via a mask. The flow of air works to maintain an open airway. Sleep Apnea sufferers must wear the mask for the entire night. One common component of a CPAP machine is a humidifier. Prior to applying the flow of air to the patient, the air is passed through the humidifier to add moisture to the air, thus helping to prevent the patient's nasal passages from drying out.

One disadvantage of existing CPAP machines is that the moist air that is provided to the patient is often stale or even has an unpleasant smell or taste. A further disadvantage is that the existing machines provide nothing more than moist air to the patient.

There is a need in the art for a CPAP machine that provides a pleasant tasting or smelling flow of air to the patient. There is a further need for a CPAP machine that is capable of providing more than just moist air.

BRIEF SUMMARY OF THE INVENTION

The present invention, in one embodiment, is a method of delivering additive with a continuous positive airway pressure ("CPAP") machine. The method includes mixing an additive with humidifier water and providing the additive to the patient with the CPAP machine. According to an alternative embodiment, the additive can be an aromatic additive or a therapeutic additive.

The present invention, in another embodiment, is an apparatus for delivering an additive to a continuous positive airway pressure ("CPAP") machine. The apparatus includes an additive delivery device associated with a reservoir of the CPAP machine. According to one embodiment, the apparatus also includes a flow control device associated with the delivery device and configured to control delivery of the additive to the CPAP machine.

In a further embodiment, the present invention is a packaged formulation for delivering an additive in a continuous positive airway pressure ("CPAP") machine. The formulation includes an additive and instructions for use of the additive with the CPAP machine. According to one embodiment, the additive is an aromatic additive or a therapeutic additive.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention relates to an improved CPAP machine and a method of providing air flow to a patient having an aromatic or therapeutic additive. The aromatic additive provides a pleasant aroma to the air flow delivered to the patient, thus eliminating any unpleasant smell or taste associated with the air delivered by the CPAP machine. Further, the therapeutic additive allows the patient to receive treatment not only for Sleep Apnea, but also for any other illness that can be treated by inhalation of an appropriate substance.

Figure 1:
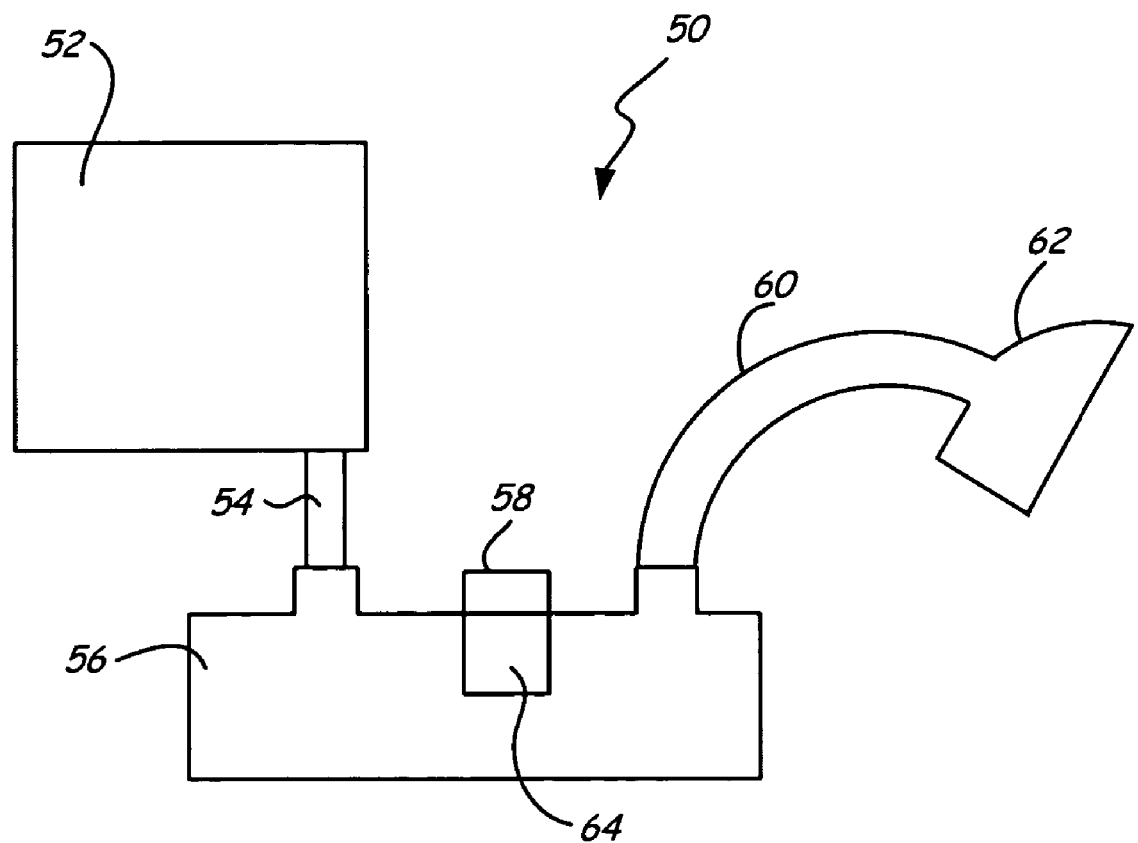
FIG. 1 is a schematic diagram of a CPAP machine, according to one embodiment of the present invention.

FIG. 1 depicts a CPAP machine 50 according to one embodiment of the present invention. The machine 50 has a flow generator 52, a reservoir 56, and a mask 62. The metering component 64 has an inlet port 58 connected to reservoir 56. A tube 54 connects the flow generator 52 to the reservoir 56, and a tube 60 connects the reservoir 56 to the mask 62.

According to one embodiment, the flow generator 52 is configured to create an air flow that is provided to the reservoir 56 and then the mask 62 via the tubes 54, 60. The flow generator 52 can be any known flow generator for a CPAP machine.

In accordance with one aspect of the invention, the additive is added to the reservoir 56 through the inlet port 58. According to one embodiment, a metering component 64 is configured to deliver the additive over time to the reservoir 56 at a metered or regulated rate. That is, the metering component 64 is configured to regulate or control over time the amount of additive that is delivered to the reservoir 56. In one aspect of the invention, the metering component 64 is a metering dial similar to the device used to control intravenous injection flow rates. That is, the additive is placed into a flow line that passes through the dial and is regulated by turning the dial to pinch or open the line, thereby regulating the amount of additive that can pass through.

Alternatively, the metering component 64 is a ball-valve system, in which a canal that allows flow of the additive can be blocked by a ball in the canal. The ball is configured to have at least one hole in it, and the ball can be turned by use of a handle connected to the ball. When the ball is turned so that the hole creates a passage in the canal, flow of the additive through the canal occurs. When the ball is turned so that the canal is completely blocked, flow of the additive is blocked. Further, the amount of flow can be regulated by regulating the size of the passage by controlling how much the ball is turned in the canal. Further, this device can be turned to provide various sized holes, thus allowing the additive to flow through to the reservoir 56 at a controlled rate. In a further alternative, any known system for timed metering or regulation of the flow of a fluid can be used with the present invention. In yet another alternative, the additive is delivered directly to the reservoir 56 without any metering or flow regulation.

The reservoir 56, in accordance with one embodiment, is configured to hold water and receive into the water the additive delivered through the inlet port 58. Thus, the reservoir 56 is configured to allow the mixing of the additive into the water. Air flow passes through the reservoir 56 from the flow generator 52 to the mask 62. The reservoir 56 is configured to allow the air flow to take up moisture in the form of the water and additive (be "humidified" with the water and additive) and further allow that air flow to pass out of the reservoir 56 and to the mask 62. The reservoir 56 can be any known reservoir used with CPAP machines to humidify air flow.

The mask 62 is configured to be placed on the patient's face and deliver the humidified air flow with the additive to the patient in such a fashion as to prevent Sleep Apnea. The mask 62 can be any known mask for use with CPAP machines to deliver the air flow to the patient.

In use, according to one embodiment of the present invention, an aromatic additive is added to the inlet port 58. The additive is in concentrate form. Alternatively, the additive is in pre-mixed form. In a further alternative, the additive is in any form capable of being added to the CPAP machine.

The aromatic additive, in accordance with one aspect of the invention, is a fragrance. The additive can be chosen from, but is not limited to, any of the following aromatic additives, including lilac, evergreen, menthol, jasmine, eucalyptus, floral, lemon, lime, orange, tangerine, peppermint, strawberry, cherry, anise, honey, mint, vanilla, mocha. Alternatively, the aromatic additive is any known pleasant fragrance that can make the air flow more pleasant for the patient.

The air flow is generated by the flow generator 52 and provided to the reservoir 56. The aromatic additive is added to the reservoir 56. The additive is delivered in a timed metering fashion or by any other method of flow regulation. Alternatively, the additive is delivered without flow regulation. The rate of delivery or the amount of the additive will vary depending on the additive and the size of the reservoir. As the air flow passes through the reservoir 56, the air is "humidified." That is, a portion of the water and aromatic additive is taken up by the air and is delivered as a humidified air flow to the mask 62.

According to an alternative embodiment of the present invention, a therapeutic additive is added to the reservoir 56. The additive is in concentrate form. Alternatively, the additive is in pre-mixed form. In a further alternative, the additive is in any form capable of being added to the CPAP machine.

The therapeutic additive, in accordance with one aspect of the invention, is any substance with therapeutic effect that can be administered by inhalation. The additive can be chosen from, but is not limited to, any substance that treats any of the following ailments or illnesses, including sinus ailments, throat ailments, chest ailments, headaches, allergies, flu, cold, menstrual cramps, and insomnia. Further, the additive can be chosen from, but is not limited to, any of the following therapeutic substances, including antihistamines, decongestants, anti-inflammatories, anti-depressants, vitamins, glucose, and chloraseptics. Alternatively, the therapeutic additive is any known substance having therapeutic effects that can be administered to the patient by inhalation.

Several exemplary therapeutic additives, which shall not be considered limiting, include such respiratory-related, flu-related, and cold-related medications as products sold under brand names such as Robitussin®, Vicks®, TheraFlu®, Sudafed®, Contact®, Comtrex®, ZICAM®, Alka Seltzer®, Advil®, and Aleve®. Non-limiting exemplary additives for allergy relief, including some prescription medications, include certain products sold under brand names such as Chlor-Trimetor®, Advil®, Benadryl®, Claritin-D®, Claritin®, Allegra®, Nasacort®, Nasanex®, and Zyrtec®. Non-limiting exemplary additives for pain relief, including some prescription medications, include certain products sold under brand names such as Tylenol®, Motrin®, Advil®, Excedrin®, Aleve®, Celebrex®, Vioxx®, Flextra-DS®, Fioricet®, and Tramadol®. Non-limiting exemplary additives for menstrual relief include certain products sold under the brand name Pamprin®. Non-limiting exemplary additives for women's health, including some prescription medications, include certain products sold under such brand names as Ortho Tri-Cyclen®, Nordette 28®, Triphasil®, Diflucan®, and Estradiol®. Non-limiting exemplary sleep aid additives, including some prescription medications, include certain products sold under such brand names as Unisom®, Ambier®, and Sonata®. Non-limiting exemplary additives for arthritic relief include certain products sold under the brand name Tylenol®. Non-limiting exemplary vitamin additives include all known vitamins such as A, B-12, C, E, etc. Non-limiting exemplary vitamin additives include certain products sold under such brand names as Centrum®, Rexall®, Sundown®, Nature Made®, Natures Valley®, and Swanson Health®. Non-limiting exemplary additives for relief from viruses and/or infections, including some prescription medications, include such products as penicillin and amoxicillin. Non-limiting exemplary muscle-relaxant additives, including some prescription medications, include products sold under such brand names as Skelaxin®, Soma®, Flexeril®, and Zanflex®. Non-limiting exemplary additives for anxiety or depression, including some prescription medications, include products under such brand names as Buspar®, Paxil®, Prozac®, Zoloft®, Wellbutrin®, and Celexa®. Non-limiting exemplary skin care additives, including some prescription medications, include products such as retin A and products under such brand names as Renova®. Non-limiting exemplary additives for sexual or genital health, including some prescription medications, include products under such brand names as Acyclovir® and Valtrex®. Non-limiting exemplary smoke-cessation additives, including some prescription medications, include products under the brand name Zyban®.

The air flow is generated by the flow generator 52 and provided to the reservoir 56. The therapeutic additive is added to the reservoir 56. The additive is delivered in a timed metering fashion or by any other method of flow regulation. Alternatively, the additive is delivered without flow regulation. The rate of delivery or the amount of the additive will vary depending on the prescribed application of the additive and the size of the reservoir. As the air flow passes through the reservoir 56, the air is "humidified." That is, a portion of the water and therapeutic additive is taken up by the air and is delivered as a humidified air flow to the mask 62.

In accordance with one alternative aspect of the invention, any aromatic or therapeutic additive disclosed herein can be added to the reservoir of any existing CPAP machine. The additive is provided in pre-mixed form. Alternatively, the additive is provided in concentrate form. In a further alternative, the additive is in any form capable of being added to the reservoir of any existing CPAP machine.

Figure 2:
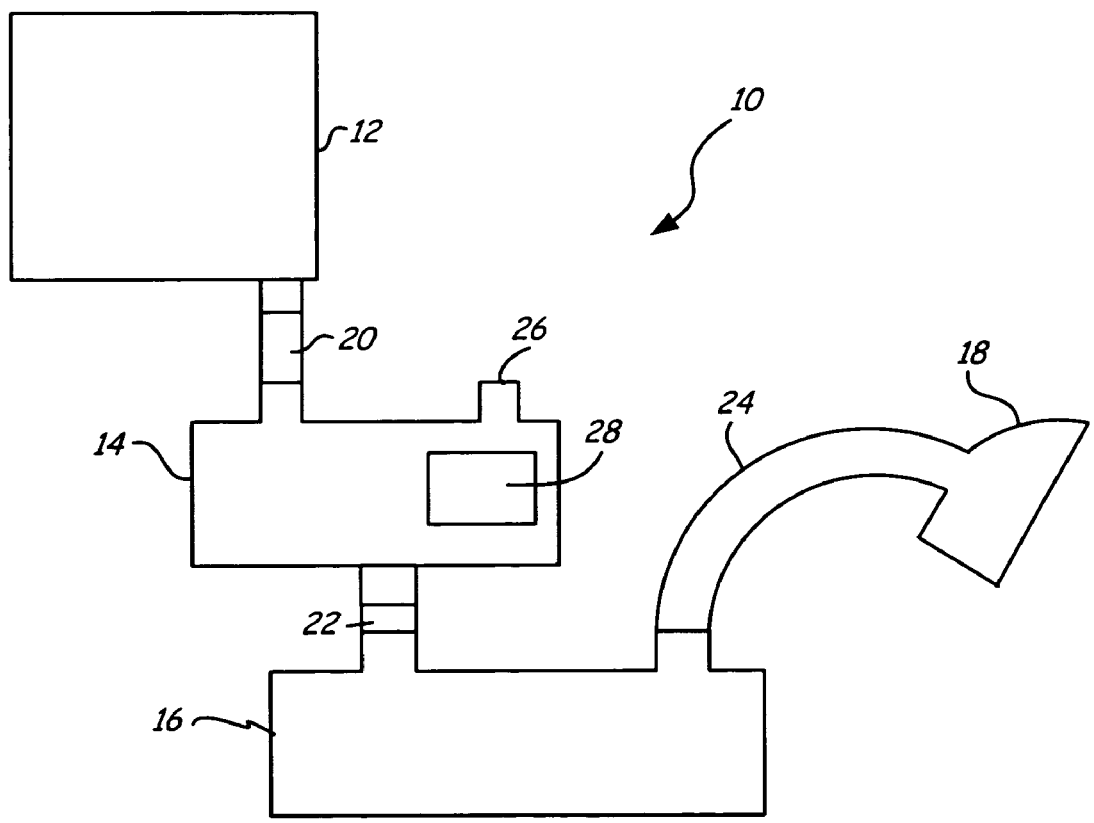
FIG. 2 is a schematic diagram of a CPAP machine, according to an alternative embodiment of the present invention.

FIG. 2 depicts a CPAP machine 10 according to an alternative embodiment of the present invention. The machine 10 has a flow generator 12, a delivery component 14, a reservoir 16, and a mask 18. The delivery component 14 has an inlet port 26 and a metering component 28. A tube 20 connects the flow generator 12 to the delivery component 14, while a tube 22 connects the delivery component 14 to the reservoir 16, and a tube 24 connects the reservoir 16 to the mask 18.

According to one embodiment, the flow generator 12 is configured to create an air flow that is provided through the delivery component 14 to the reservoir 16 and then the mask 18 via the tubes 20, 22, 24.

The delivery component 14, according to one embodiment, is configured to receive an additive and deliver the additive to the reservoir 16. The delivery component 14 is connected to the flow generator 12 by the tube 20 and receives air flow from the generator 12 through the tube. In accordance with one aspect of the invention, the additive is added to the delivery component 14 through the inlet port 26. The additive is then mixed with the air flow and delivered to the reservoir 16 through the tube 22. Alternatively, the additive is delivered through the tube 22 to the reservoir 16 separately from the air flow.

The delivery component 14, according to one embodiment, is configured to deliver the additive over time to the reservoir 16 at a metered or regulated rate using the metering component 28. That is, the metering component 28 is configured to regulate or control over time the amount of additive that is delivered to the reservoir 16. In one aspect of the invention, the metering component 28 is a metering dial similar to the device used to control intravenous injection flow rates, as discussed above. Alternatively, the metering component 28 is a ball-valve system, as discussed above. In a further alternative, any known system for timed metering or regulation of the flow of a fluid can be used with the present invention. In yet another alternative, the additive is delivered directly to the reservoir 16 without any metering or flow regulation.

The reservoir 16, in accordance with one embodiment, is configured as disclosed above. The reservoir 16 can be any known reservoir used with CPAP machines to humidify air flow.

The mask 18, according to one aspect of the invention, is configured as described above. The mask 18 can be any known mask for use with CPAP machines to deliver the air flow to the patient.

In use, according to one embodiment of the present invention, an aromatic additive as described above is added to the delivery component 14. The air flow is generated by the generator 12 and provided to the delivery component 14 and then to the reservoir 16. The aromatic additive is added to the delivery component 14 and then delivered to the reservoir 16. The additive is delivered in a timed metering fashion or without flow regulation. The rate of delivery or the amount of the additive will vary depending on the additive and the size of the reservoir. As the air flow passes through the reservoir 16, the air is "humidified." That is, a portion of the water and aromatic additive is taken up by the air and is delivered as a humidified air flow to the mask 18.

According to an alternative embodiment of the present invention, a therapeutic additive as described above is added to the delivery component 14. The air flow is generated by the generator 12 and provided to the delivery component 14 and then to the reservoir 16. The therapeutic additive is added to the delivery component 14 and then delivered to the reservoir 16. The additive is delivered in a timed metering fashion or by any other method of flow regulation. Alternatively, the additive is delivered without flow regulation. The rate of delivery or the amount of the additive will vary depending on the prescribed application of the additive and the size of the reservoir. As the air flow passes through the reservoir 16, the air is "humidified." That is, a portion of the water and therapeutic additive is taken up by the air and is delivered as a humidified air flow to the mask 18.

Although the present invention has been described with reference to preferred embodiments, persons skilled in the art will recognize that changes may be made in form and detail without departing from the spirit and scope of the invention.

What is claimed is:

1. A method of delivering additive with a continuous positive airway pressure ("CPAP") machine comprising:
   mixing a solid or liquid additive with water in a humidifier using an additive delivery device;
   introducing air flow past the humidifier such that the air flow takes up moisture in the form of the water and the additive;
   passing moisture-added air flow out of the humidifier; and
   providing the moisture-added air flow having the additive to the patient with the CPAP machine.

2. The method of claim 1 wherein the additive is an aromatic additive.

3. The method of claim 1 wherein the additive is a therapeutic additive.

4. An apparatus for delivering an additive to a continuous positive airway pressure ("CPAP") machine comprising:
   a fluid reservoir for holding a fluid and configured with an air flow inlet and an air flow outlet, such that an air flow passes into the fluid reservoir, takes up the moisture from the reservoir, and passes out of the fluid reservoir; and
   an additive delivery component arranged on the fluid reservoir, the delivery component comprising:
      an additive inlet port coupled to the fluid reservoir for introducing the additive to the fluid reservoir and arranged distal to the air flow inlet and air flow outlet; and
      a metering component in fluid communication with the additive inlet port, the metering component configured to meter the additive to the fluid in the fluid reservoir.

5. The apparatus of claim 4 wherein the additive is an aromatic additive.

6. The apparatus of claim 4 wherein the additive is a therapeutic additive.

7. The apparatus of claim 4 wherein the delivery component is integral with the reservoir.

8. The apparatus of claim 4 wherein the delivery component is operably coupled with the reservoir by a tube.

* * * * *